United States Patent [19]
Gruber et al.

[11] Patent Number: 5,925,682
[45] Date of Patent: Jul. 20, 1999

[54] EPINEPHRINE AS INHIBITOR OF CANCEROUS TUMORS

[75] Inventors: Paul K. Gruber, Woodbury; Jan Geliebter, Brooklyn, both of N.Y.

[73] Assignee: Immunotech Inc., Woodbury, N.Y.

[21] Appl. No.: 08/751,336

[22] Filed: Nov. 18, 1996

Related U.S. Application Data

[63] Continuation-in-part of application No. 08/560,862, Nov. 20, 1995, abandoned.
[51] Int. Cl.$^6$ .................................................. A61K 31/135
[52] U.S. Cl. ............................................................. 514/653
[58] Field of Search ...................................... 514/653, 649

[56] References Cited

PUBLICATIONS

Drott, C., et al., "Cardiovascular and metabolic response to adrenaline infusion in weight–losing patients with and without cancer", *Clinical Physiology*, vol. 9, pp. 427–439 (1989).

Van Den Brenk, H.A.S., et al., "Lowering of innate resistance of the lungs to the growth of blood–borne cancer cells in states of topical and systemic stress", *Br. J. Cancer*, vol. 33, p. 60 (1976).

Ensminger, William D., et al., "Regional chemotherapy of neoplastic diseases", *Pharmac. Ther.*, vol. 21, pp. 277–293 (1983).

Weiner, "Norepinephrine, epinephrine, and the sympathomimetic amines", *Goodman and Gibson's the Pharmaceutical Basis of Therapeutics*, 8th Edition, Chapter 8, pp. 138–157 (1990).

Hoffmann, B.B., et al., "Adrenergic receptor antagonists", *Goodman and Gilson's The Pharmacological Basis of Therapeutics*, 8th Edition, Chapter 11, pp. 221–243 (1990).

Ganog, W.F., ed., *Review of Medical Physiology*, "The adrenal medulla & adrenal cortex", Chapter 20, pp. 323–347 (1993).

Sato, T., et al., Dialog Computerized Abstract of Japanese Journal Article "Itra–arterial chemotherapy with nor–adrenaline experimental study," *Gan to Kagaku Ryohu* (Japan) 12 (6) pp. 1245–1252 (Jun. 1985).

Dyer, An Index of Tumor Chemotherapy, Wilt, Mar. 1949, pp. 10–12 and 165.

Carter et al, Chemotherapy of Cancer, 2$^{nd}$ Ed, 1981 John Wiley & Sons, N.Y., N.Y., pp. 362–365.

*Primary Examiner*—Jerome D Goldberg
*Attorney, Agent, or Firm*—Hoffmann & Baron, LLP

[57] ABSTRACT

A method for reducing cancerous tumors is disclosed. The method includes administering to a mammal an effective amount of epinephrine. In another embodiment, the mammal is immediately immobilized after receiving injections of epinephrine. In a most preferred embodiment, the method also includes administering an effective amount of a cardioselective adrenergic blocking agent prior to administering of epinephrine.

3 Claims, 11 Drawing Sheets

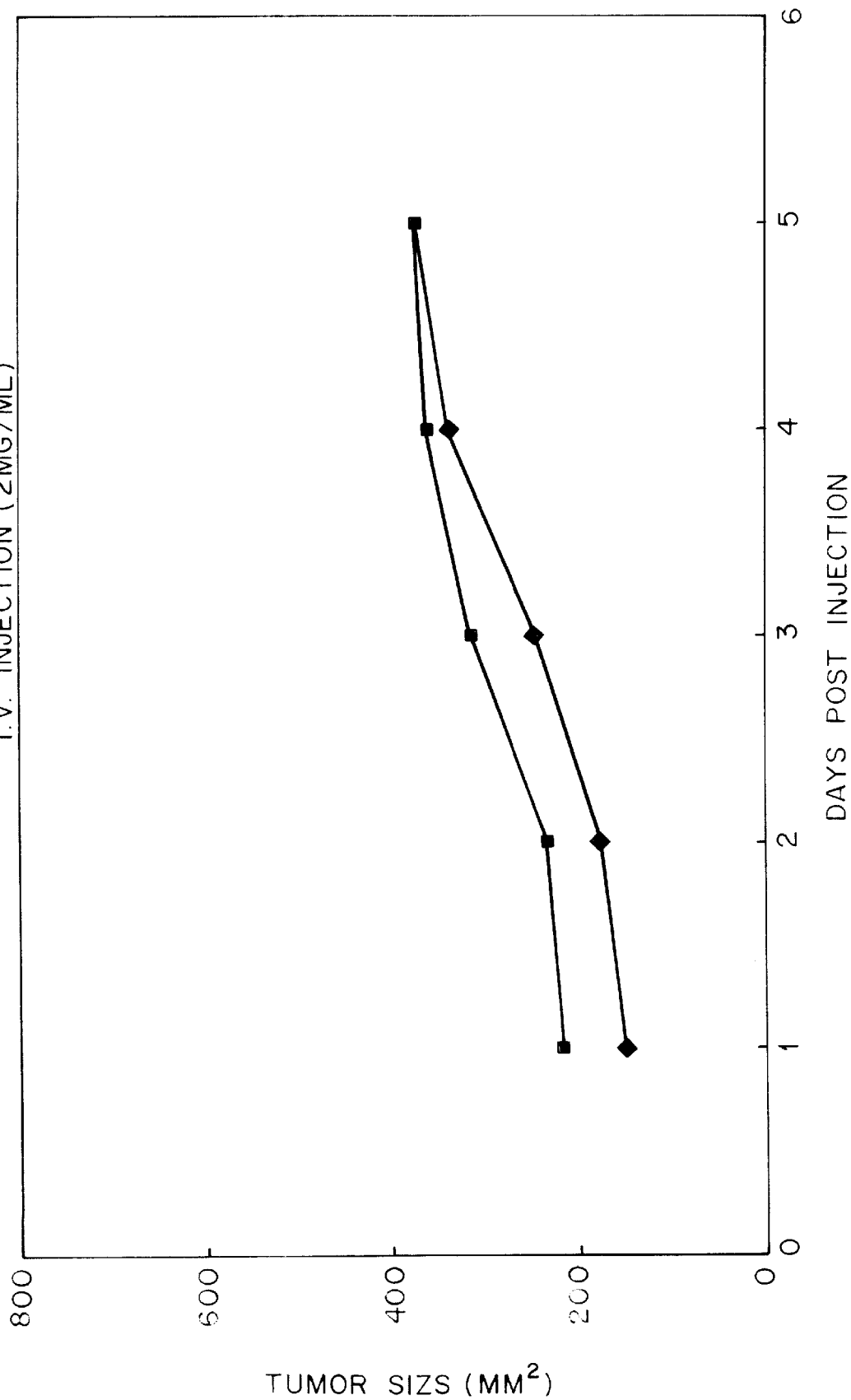

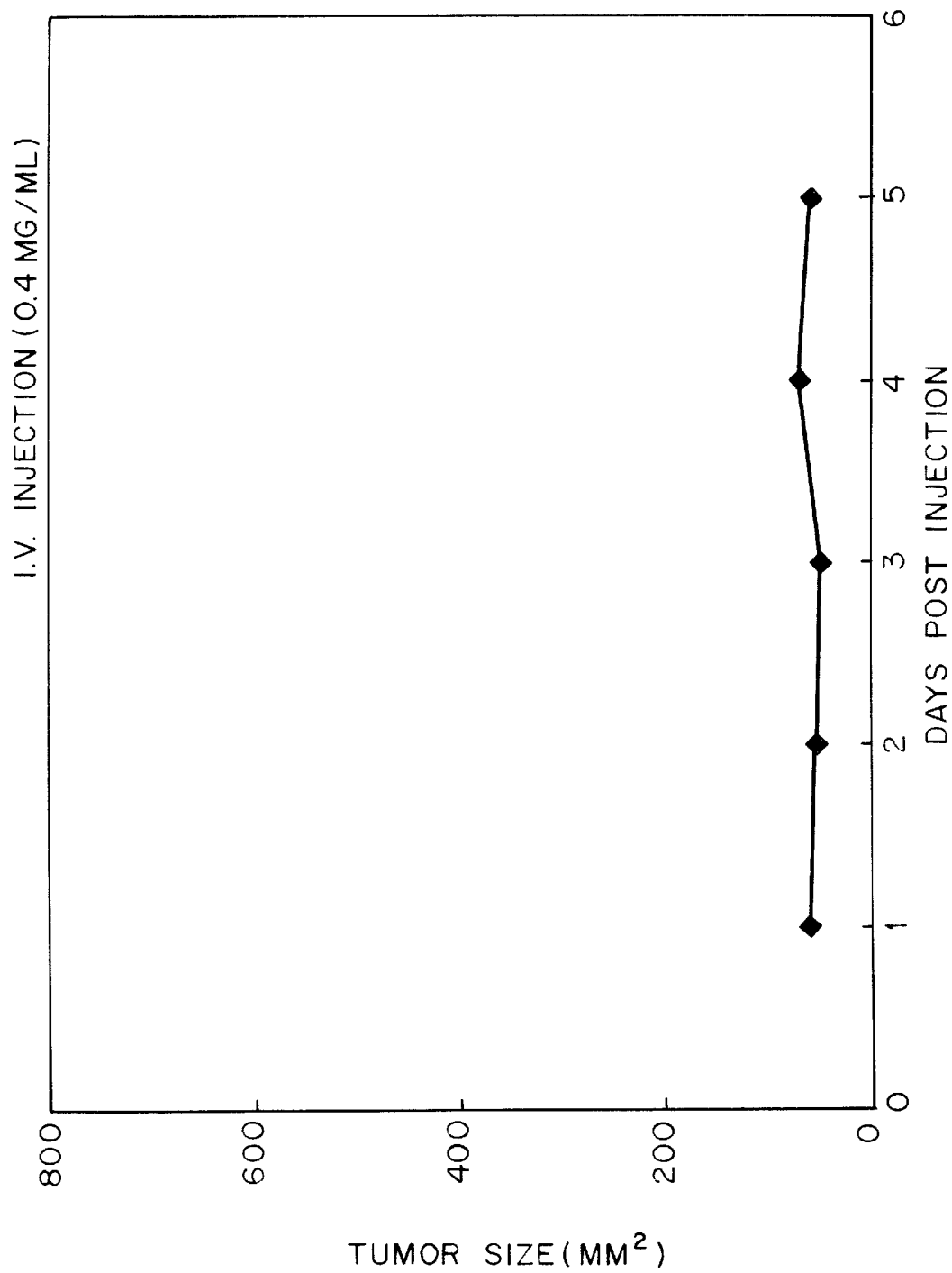

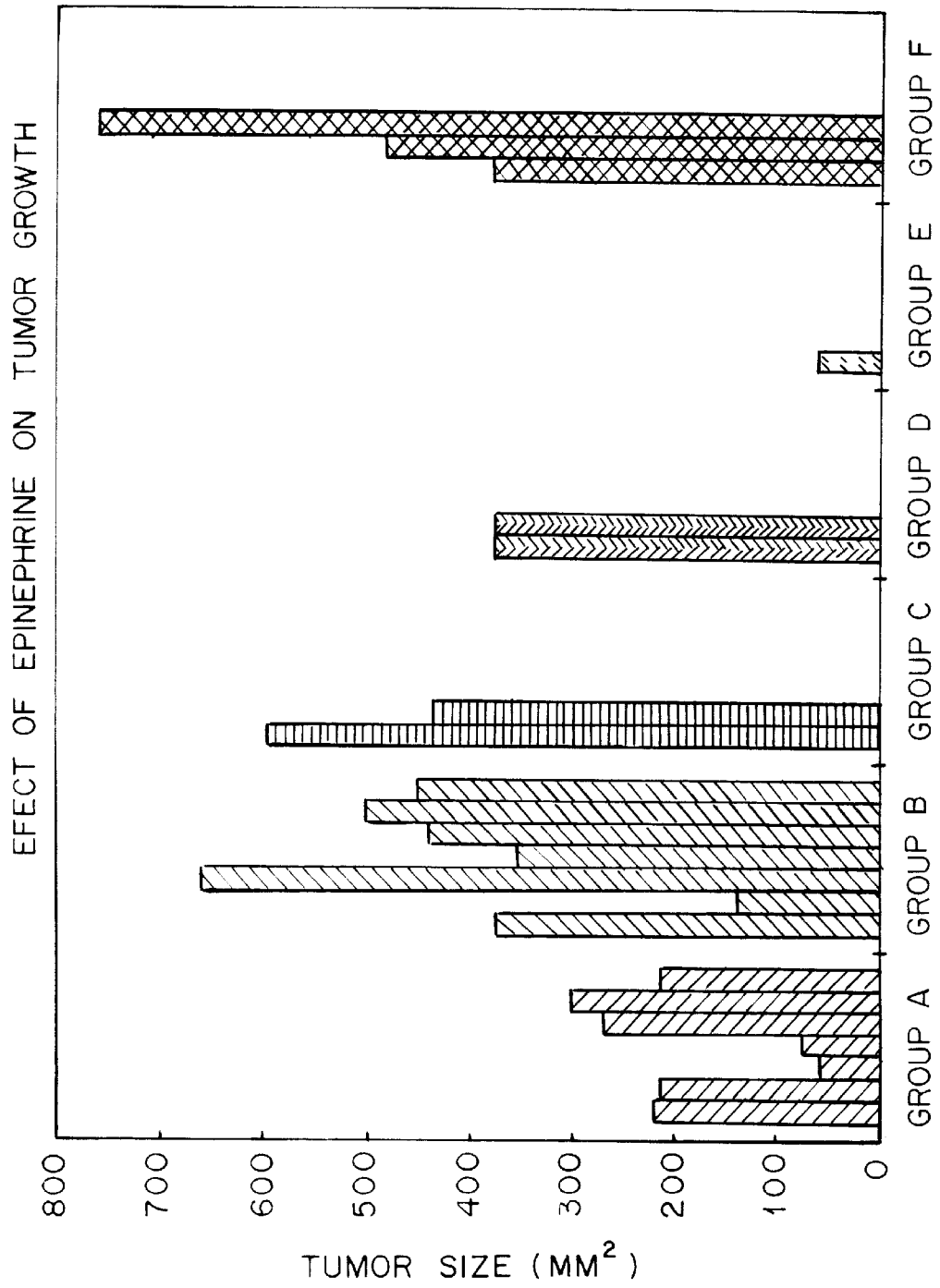

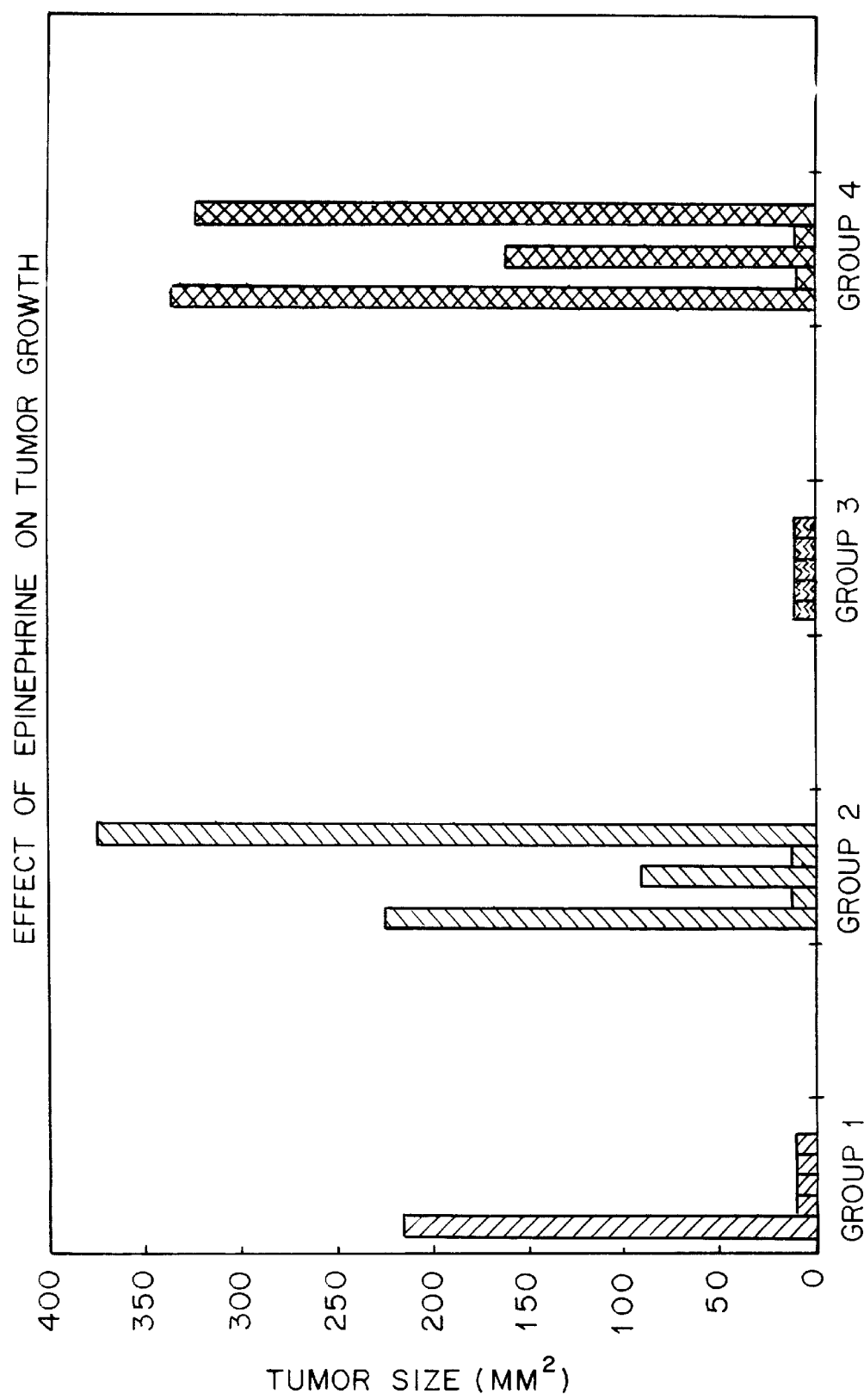

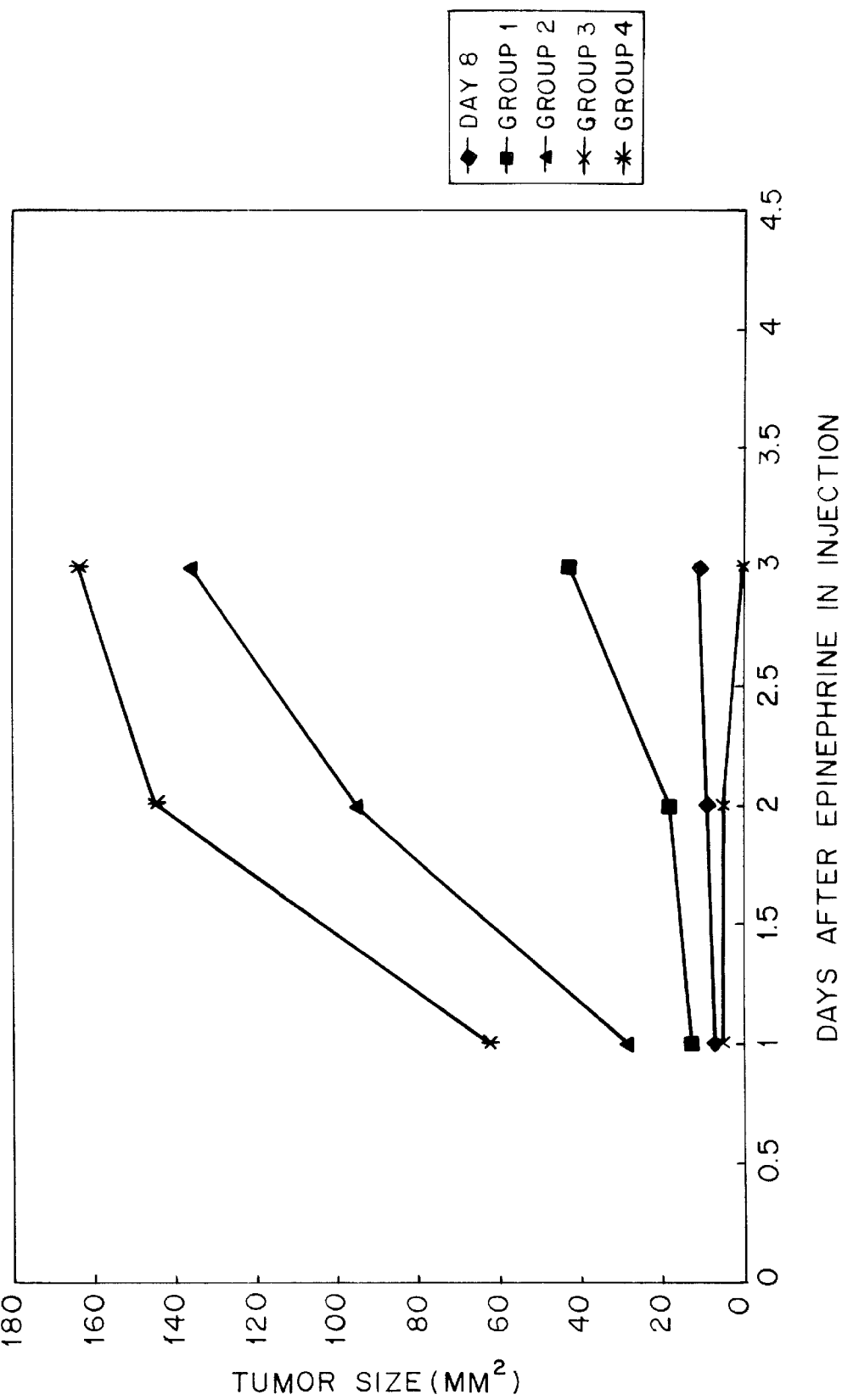

5,925,682

EPINEPHRINE AS INHIBITOR OF CANCEROUS TUMORS

This application is a continuation-in-part of application Ser. No. 08/560,862, filed on Nov. 20, 1995, now abandoned.

BACKGROUND OF INVENTION

1. Field of the Invention

This invention relates to a method of inhibiting the growth of cancerous tumors. More specifically, the invention provides a method of significantly reducing tumorous growth by injecting a mammal with an effective amount of epinephrine.

2. Background of the Related Art

In recent years, considerable research has been conducted on finding treatment for cancer. Each year over a million Americans are diagnosed with cancer. Traditional treatments such as surgery, chemotherapy, radiation therapy, hormonal therapy and immunotherapy have an important role in the treatment of many cancers, yet the response to such treatments depends to a large extent on the type of tumor, its size, and whether or not it has spread. Despite important scientific and medical advances in traditional cancer treatments, more than half a million Americans die from cancer each year.

Accordingly, there is still a continuing need for more effective therapies which could be used by themselves or together with traditional treatments to fight cancer.

It is therefore, a purpose of the present invention to provide a new method for treatment of malignant tumors.

SUMMARY OF THE PRESENT INVENTION

These and other objectives and purposes are satisfied by the present invention which provides a new method for treatment of malignant tumors by injecting a patient with an effective dosage of epinephrine.

The method provided by the present invention includes administering an effective amount of epinephrine into a patient either intravenously or intraperitoneally. In a preferred embodiment, epinephrine is administered intraperitoneally or intravenously into a mammal having malignant tumors. In another preferred embodiment, the mammal is immobilized during the administration of epinephrine for 60 seconds. In a most preferred embodiment, an effective amount of metaprolol is administered prior to the administration of epinephrine. To achieve a decrease in the growth of cancerous tumors, the dosage of epinephrine which can be intravenously or intraperitoneally injected into a patient varies from about 1 to about 500 micrograms in 10 ml and preferably from about 10 micrograms to about 500 micrograms in 10 ml per body weight of 75 kg.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 2 illustrates the effect of various concentrations of epinephrine on tumor growth three days after injection with epinephrine for each mouse in groups A, B, C, D, E and F, respectively.

FIGS. 4a and 4b illustrate the effect of epinephrine on tumor growth of mice which were subcutaneously injected with 50,000 BW5147 cells in the right flank.

FIG. 5 illustrates the effect of epinephrine on tumor growth as an average tumor burden for groups 1, 2, 3, 4 on days 7, 9 and 11 after epinephrine injection.

DETAILED DESCRIPTION OF THE INVENTION

Figure 1A:
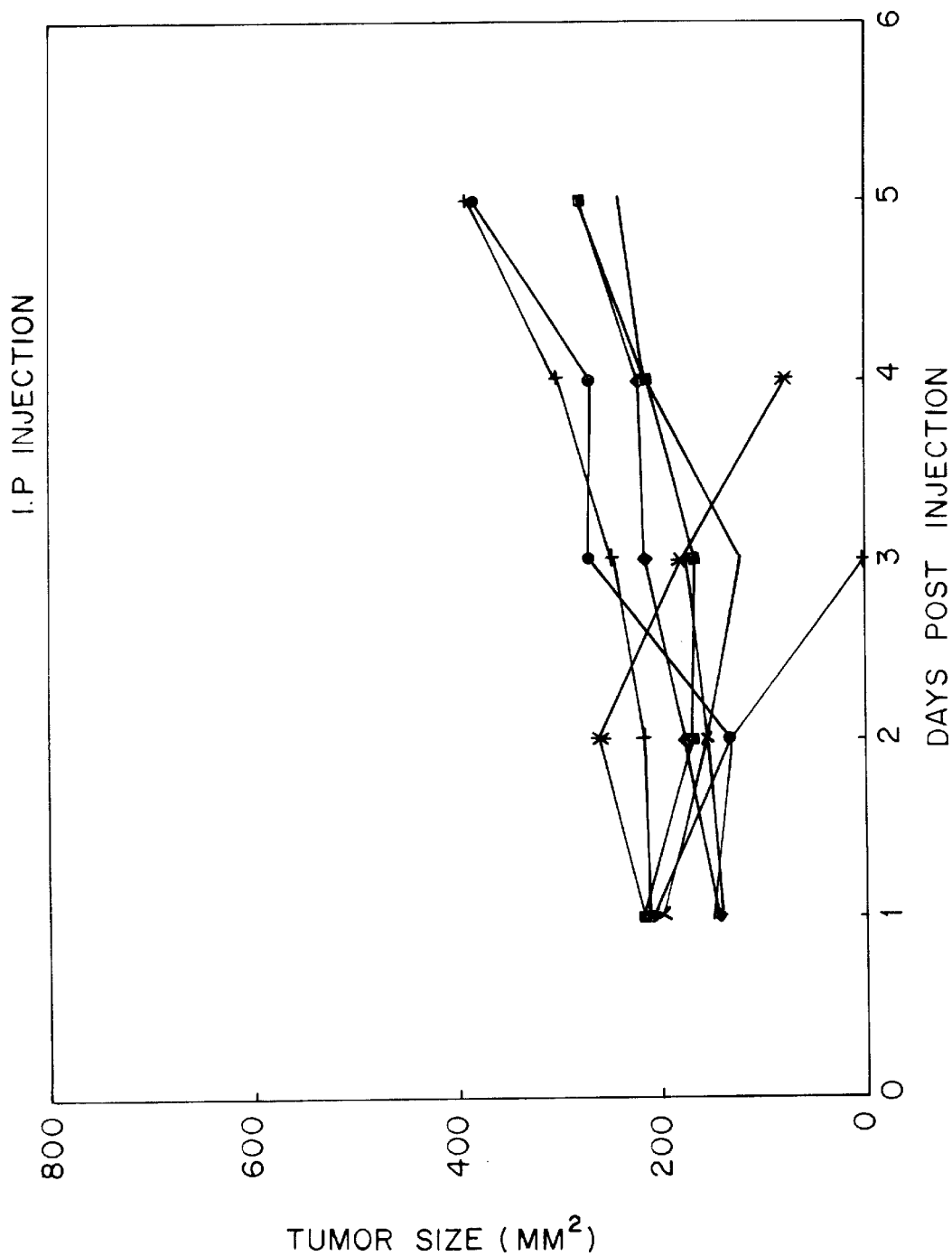
FIG. 1 illustrates the effect of various concentrations of epinephrine on tumor growth for each mouse in groups A, B, C, D, E and F respectively. Each symbol in FIGS. 1(a)–1(f) represents the tumor size value for an individual mouse.

The present invention provides a new method of inhibiting the growth of cancerous tumors in mammals. Because the immobilization of mammals immediately alters the level of plasma epinephrine for extended periods of time, the method of the invention includes introducing adrenaline or epinephrine intravenously or intraperitoneally while simultaneously restraining or limiting the body of the mammal from physical movement for 60 seconds.

Produced in the adrenal medulla by the methylation of norepinephrine, epinephrine is formed by the hydroxylation and decarboxylation of tyrosine. The biological effects of epinephrine include glycogenolysis in liver and skeletal muscle, mobilization of free fatty acids, increased plasma lactate and glucose, the stimulation of the metabolic rate, increased hepatic blood flow, decreased excretion of sodium, potassium, chloride, and the inhibition of insulin secretion.

The biologic and pharmacologic effects of epinephrine are brought about by its binding to the $\alpha$- and $\beta$-adrenergic receptors. There are two a receptors, $\alpha 1$ and $\alpha 2$, and three $\beta$ receptors, $\beta 1$, $\beta 2$ and $\beta 3$. Generally, $\beta 1$ adrenergic receptors predominate in cardiac tissue while $\beta 2$ receptors are found in smooth muscle and gland cells. Alpha 1 receptors are the most common receptor at postsynaptic effector sites of smooth muscle and gland cells, while $\alpha 2$ receptors are believed to be present on nerve terminals.

The distribution of different adrenergic receptors on different cells accounts for the multitude of effects of epinephrine. For example, the binding of epinephrine to $\beta 1$ receptors is responsible for the increase in myocardial excitability, causing extrasystoles, and sometimes cardiac arrhythmias. In contrast, epinephrine binding to $\alpha 1$ receptors results in the dilation of blood vessels in skeletal muscles and the liver. Adrenergic receptors vary in their affinity for different catecholamines. Thus, epinephrine, norepinephrine and isoproterenol will bind to different receptors and the cells that express them with different affinities and effect different responses. The selective use of specific $\alpha$ or $\beta$ blocking agents can be employed to achieve a particular response to a particular catecholamine, while eliminating unwanted effects.

The selective use of specific $\alpha$ or $\beta$ blocking agents can be employed to achieve a particular response to a particular catecholamine, while eliminating unwanted side effects caused to epinephrine users. For example, selective blockers of $\beta 1$-adrenergic receptors antagonize the actions of epinephrine on the heart, but do not block vasoconstrictor responses mediated by a receptors. In particular, prior administration of the cardioselective adrenergic blocking agent, metaprolol, significantly decreases the mean aortic blood pressure of beagle dogs that have been infused with epinephrine. (Weiner, N. in *Goodman and Gilson's The Pharmacological Basis of Therapeutics*, 6th Edition Ch. 9, (1980) and Hoffinan, B. B. and Lefkowitz, R. J. in Goodman and Gilson's *The Pharmacological Basis of Therapeutics,* 8th Edition Ch. 11, (1990). Other blocking agents include atenolol, esmolol and acebutolol.

The clinical uses of epinephrine have centered on its effects on blood vessels, the heart and bronchial muscles. It is commonly used to relieve respiratory distress due to bronchospasm, and for rapid relief from allergic reactions. The clinical dosage of intravenously administered epinephrine is usually much less than that given by intramuscular or subcutaneous injection.

The effects of intravenously injected epinephrine compared to subcutaneous injection or slow intravenous infusion are different. This is believed to be due to slow absorption of subcutaneous injected epinephrine due to the drug's local vasoconstrictor action. In fact, the effects of subcutaneously injected doses as large as 0.5 to 1.5 mg epinephrine can be duplicated by the intravenous infusion of as little as 10–30 $\mu$g/min.

The resting plasma level of epinephrine is approximately 25 pg/ml. At 50 pg/ml epinephrine causes tachycardia, at 75 pg/mi increased systolic blood pressure and lipolysis, at 150 pg/ml hyperglycemia, increased plasma lactate and decreased diastolic blood pressure. After accidental intravenous injection of subcutaneous doses, blood pressure rises to 400/300 mm Hg for short time. Cerebral hemorrhage can occur, as well as hyperventilation, pallor, and palpitation. Large doses can cause death by interference with gaseous exchange due to the development of pulmonary edema.

The half life of epinephrine in the circulatory system is about two minutes, as it is rapidly methoxylated and oxidized. In plasma, approximately 70% of epinephrine is inactive as it is conjugated to sulfates. (Ganong, W. F., ed., *Review of Medical Physiology,* ch. 20, 1993; Weiner N., in Goodman and Gilson's *The Pharmacological Basis of Therapeutics,* 8th edition, ch. 10 (1990)).

It has been unexpectedly discovered that when epinephrine was intraperitoneally or intravenously injected in small amounts in an immobilized mammal having cancerous tumors, the tumors shrunk or progressed much more slowly than in untreated mammals. In a preferred embodiment, the amount of intravenously or intraperitoneally injected epinephrine was equal to or less than 0.2 ml of 0.2 mg/ml per 20 g of body weight.

In a most preferred embodiment, the mammal is administered intravenously an effective amount of metaprolol prior to injecting epinephrine either intraperitoneally or intravenously. The amount of metaprolol would vary from about 0.1 mg to about 0.4 mg per 1000 g of body weight.

Without being bound by theory, it is believed that a small amount of intraperitoneally or intravenously administered injection of epinephrine can significantly slow the growth of pre-existing tumors. As the immobilization of laboratory mammals has been shown to alter immediately the level of plasma epinephrine for extended periods of time, the immobilization of a mammal who has received small amounts of intraperitoneally or intravenously administered epinephrine is also believed to enhance the retardation of cancerous growth observed in mammals treated according to the method of the present invention. Furthermore, it is also believed that by administering a cardioselective adrenergic blocking agent such as metaprolol prior to injecting epinephrine, possible deleterious side effects of epinephrine on the cardiovascular system can be avoided.

The focus of the following examples is to illustrate the effect of intraperitoneally or intravenously injected epinephrine on immobilized mice which have been previously injected with tumor cells.

EXAMPLES

The following examples further illustrate the present invention but are not meant in any way to restrict the scope of the invention.

MATERIALS AND METHODS

AKR/J mice were obtained from the Jackson Laboratories in Bar Harbor, Me. and housed at the SUNY at Stony Brook animal facility. BW 5147, a T cell lymphoma derived from AKR/J mice, was obtained from the American Type Culture Collection (Rockville, Md.). BW 5147 cells were maintained in Dulbecco's Modified Eagle's Medium (DMEM) modified with 10% fetal calf serum. Epinephrine hydrochloride was purchased from Sigma Chemical Co. in St. Louis, Mo.

Cultured tumor cells were injected into the mice subcutaneously in the right flank with a 23 gauge needle. The tumor size was calculated by taking the product of the length and width of tumor. All dimensions were obtained using a Vernier caliper.

Injections of epinephrine chloride into mice were performed with a 26 gauge needle. After injections, the mice were immobilized in a 50 ml plastic conical centrifuge tube of the Falcon brand, with adequate ventilation, for one minute.

Statistical analysis on the data obtained were performed using a two-tailed two-sample t-test assuming unequal variances.

Example 1

AKR/J mice were subcutaneously injected in the right flank with one million BW5147 cells. Eleven days later, tumor sizes were measured and the mice were divided into the following six groups:

(a) Group A, consisting of eight mice, was given intraperitoneally an injection of 0.4 mg of epinephrine, in 0.2 ml of saline solution;

(b) Group B, consisting of seven mice, was injected subcutaneously (in the tail) with 0.01 mg of epinephrine, in 0.05 ml saline solution;

(c) Group C, consisting of two mice, was kept as a control group, and was left uninjected;

(d) Group D, consisting of two mice, was injected intravenously with 0.2 mg epinephrine, in 0.1 ml of saline solution;

(e) Group E, consisting of one mouse, was injected intravenously with 0.04 mg epinephrine, in 0.1 ml saline solution;

(f) Group F, consisting of three mice, was injected intravenously with 0.02 mg epinephrine, in 0.1 ml saline solution.

Figure 1B:
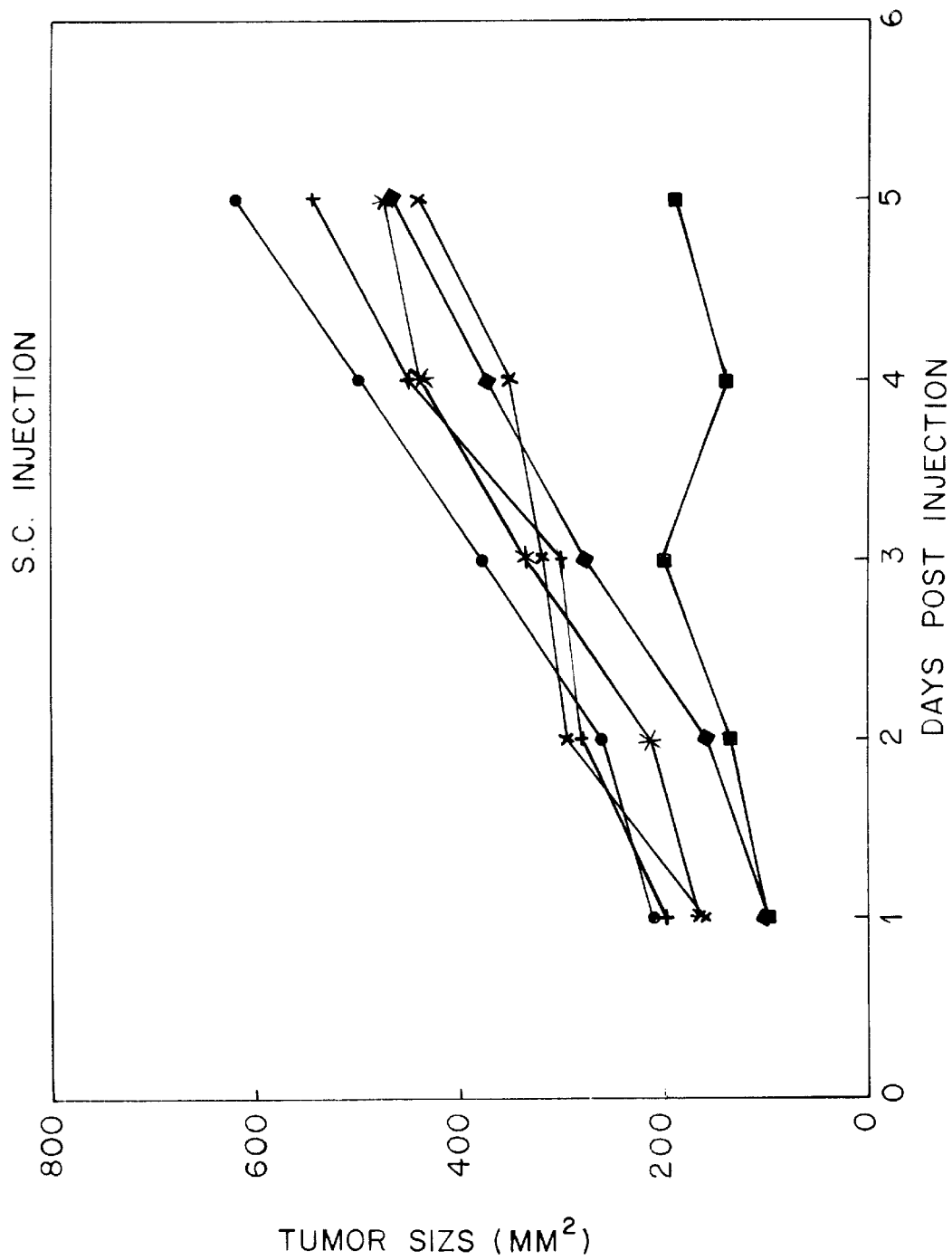
Figure 1C:
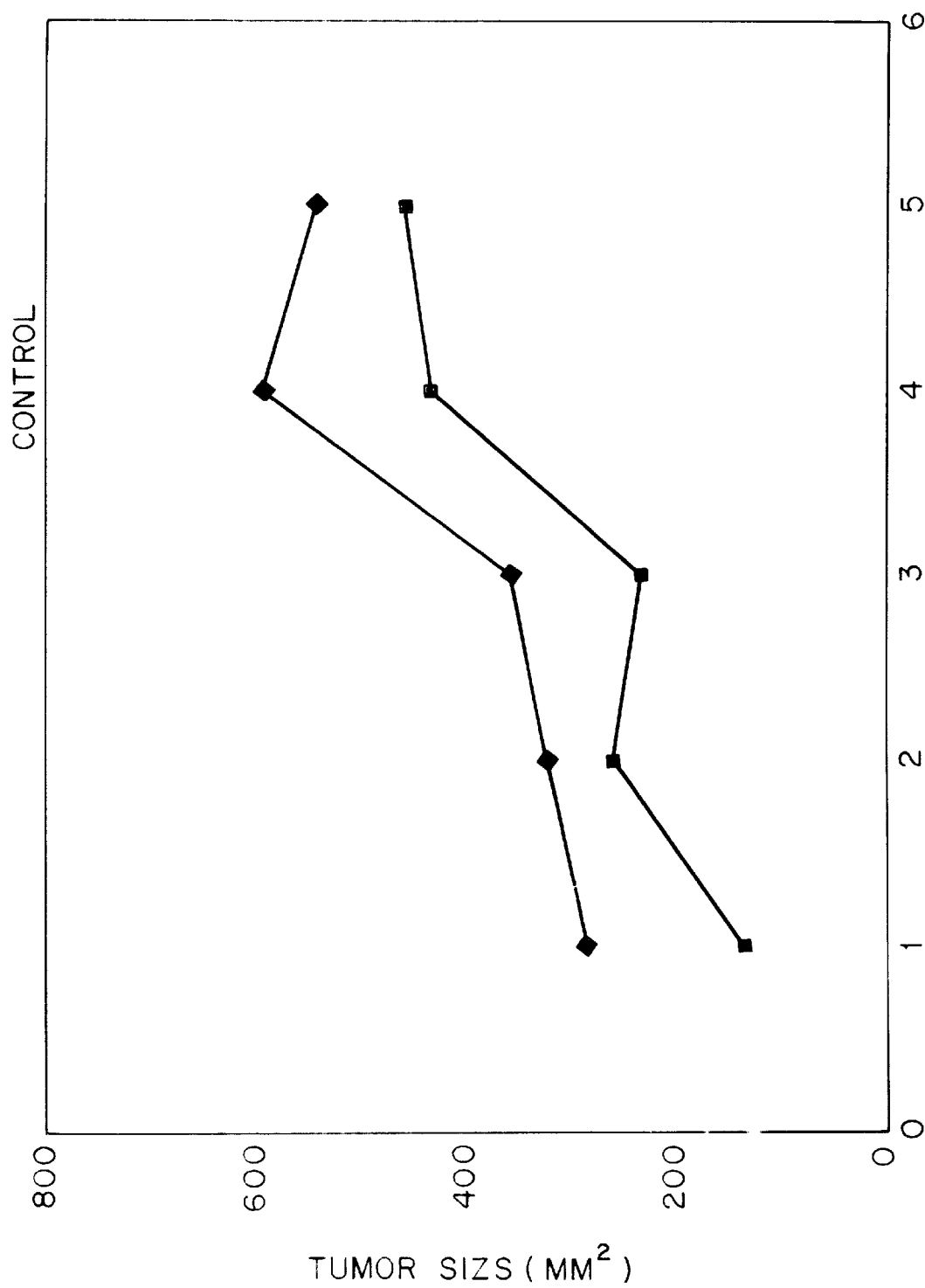

The tumor size for mice in each group was measured daily for the next five days. As indicated in FIGS. 1a to 1c, tumor size increased more slowly, or decreased in size, in the intraperitoneally injected mice of group A, as compared to the tumor size of control group C or the subcutaneously injected mice in group B. Some mice with the smallest tumors were lethargic, cold to the touch, and several died by day 3.

Figure 1F:
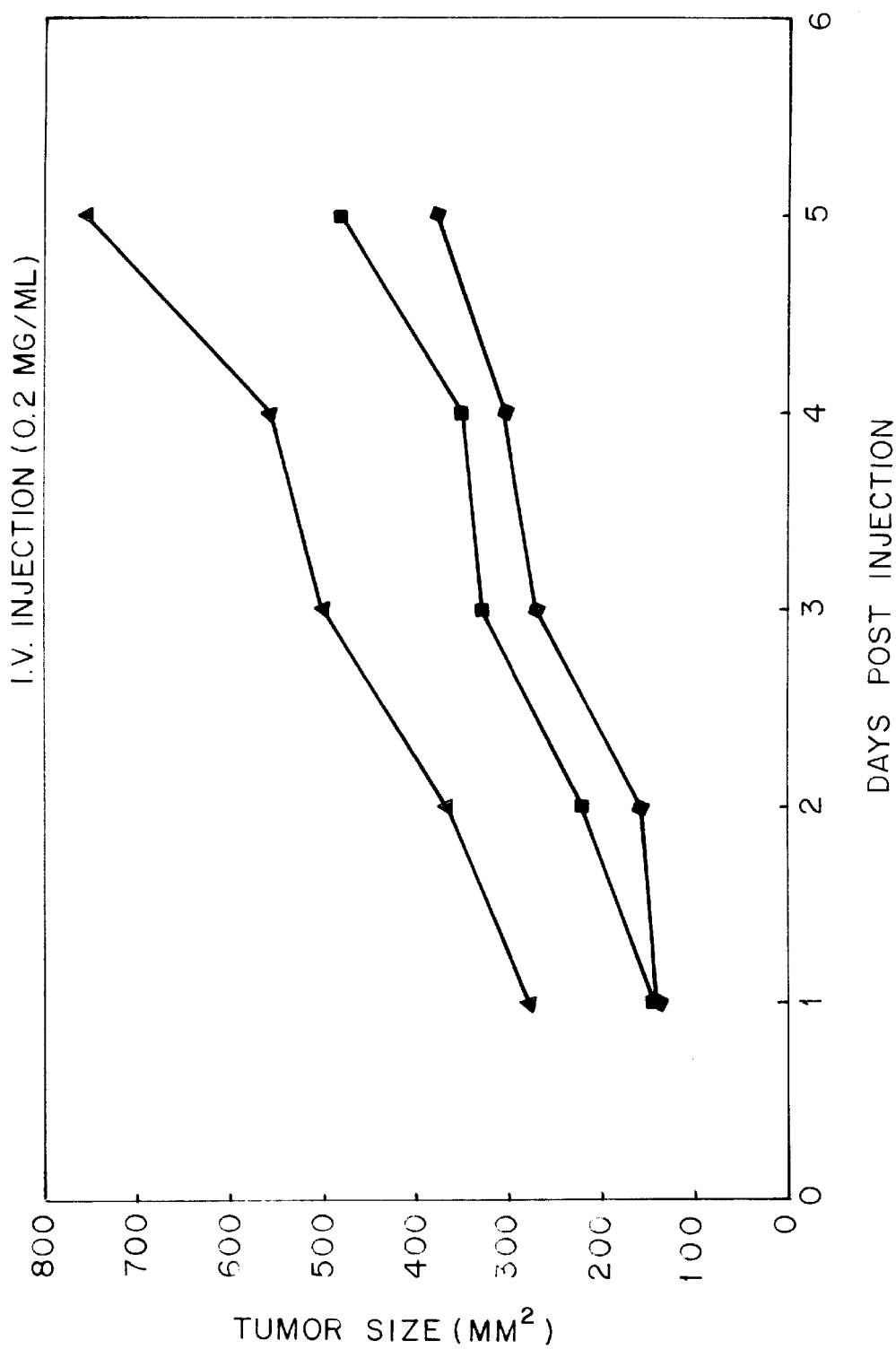

Further, mice intravenously injected with 0.2 mg epinephrine, as in Group D shown in FIG. 1d, developed tumors which progressed more slowly than mice in the control groups B, C or combined B/C, or mice injected with 0.02 mg epinephrine shown in Group F of FIG. 1f, who survived until the end of the experiment. Further, the tumor in the one mouse injected intravenously with 0.04 mg epinephrine in Group E shown in FIG. 1e did not grow.

Tumor sizes were quantitated and statistically analyzed on day 3, at which time seven of eight intraperitoneally injected mice were still alive as shown in Table 1 below.

TABLE 1

EFFECT OF EPINEPHRINE ON TUMOR GROWTH

| GROUP | TUMOR SIZE ($mm^2$ + SEM*) | STATISTICAL SIGNIFICANCE** |
|---|---|---|
| GROUP A | 194 ± 34.8 | — |
| GROUP B | 416 ± 59.1 | p < .009 |
| GROUP C | 515 ± 81.4 | p < .17 |
| GROUP B, C | 438 ± 49.0 | p < .001 |
| GROUP D | 351 | |
| GROUP E | 72 | |
| GROUP F | 405 | |

*SEM = standard error of the mean
**The statistical significance is calculated as compared to Group A, using the two-tailed two-sample t-test assuming unequal variances.

As illustrated in Table 1, Group A had a mean tumor size of 194±34.8 $mm^2$, Group B had a mean of 416±59.1 $mm^2$ and Group C had a mean of 515±81.4 $mm^2$, where these values were based on standard error of the mean. Because both Groups B and C were controls for Group A, their data was combined into a larger control group, BC. When groups B and C were combined, the mean of the new group BC was 438±49.0 $mm^2$. The decrease in tumor size in group A is very significant compared to Group B (p<0.009) and the combined BC group (p<0.001). These data are also illustrated in FIG. 2.

Figure 3:
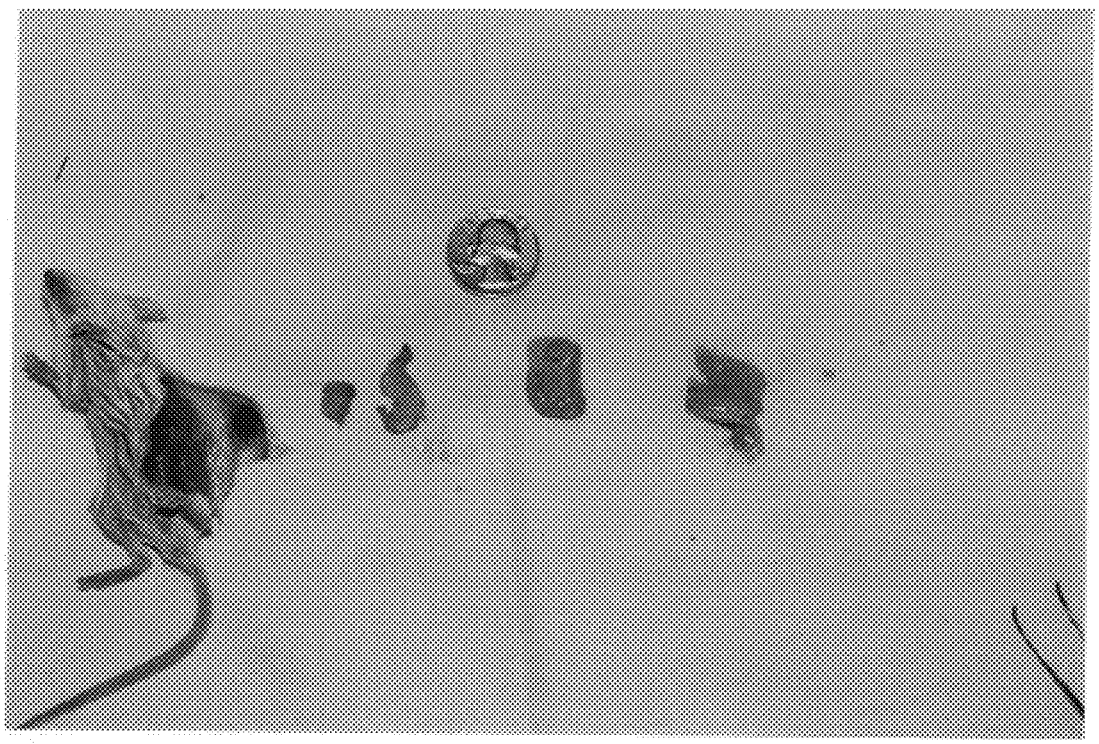
FIG. 3 illustrates resected tumors of two mice from groups A and B in relation to the size of a quarter.

Tumors were removed from two mice in Group A that died on day 3, and two representative mice from Group B. The resected tumors are shown in FIG. 3, in relation to the size of a quarter. The two tumors on the left were resected from intraperitoneally injected mice of Group A. The two tumors on the right were resected from subcutaneously injected mice of Group B. The weight of the two tumors from Group A mice were 0.19 and 0.42 grams, while tumors from Group B mice were 1.42 and 1.08 grams.

Example 2

AKR/J mice were subcutaneously injected with 50,000 BW5147 cells in the right flank. Nine days later, mice were injected intraperitoneally and intravenously with epinephrine, and tumor sizes were measured. The mice were divided into the following four groups:

(i) Group 1, consisting of five mice, was given an injection of 0.16 mg of epinephrine, in 0.2 ml saline solution;

(ii) Group 2, consisting of five mice, was injected with 0.08 mg epinephrine in 0.2 ml saline solution;

(iii) Group 3, consisting of five mice, was injected with 0.05 mg epinephrine in 0.2 ml saline solution; and (iv) Group 4, consisting of five mice, was not injected with epinephrine and constituted the control group.

Figure 4B:
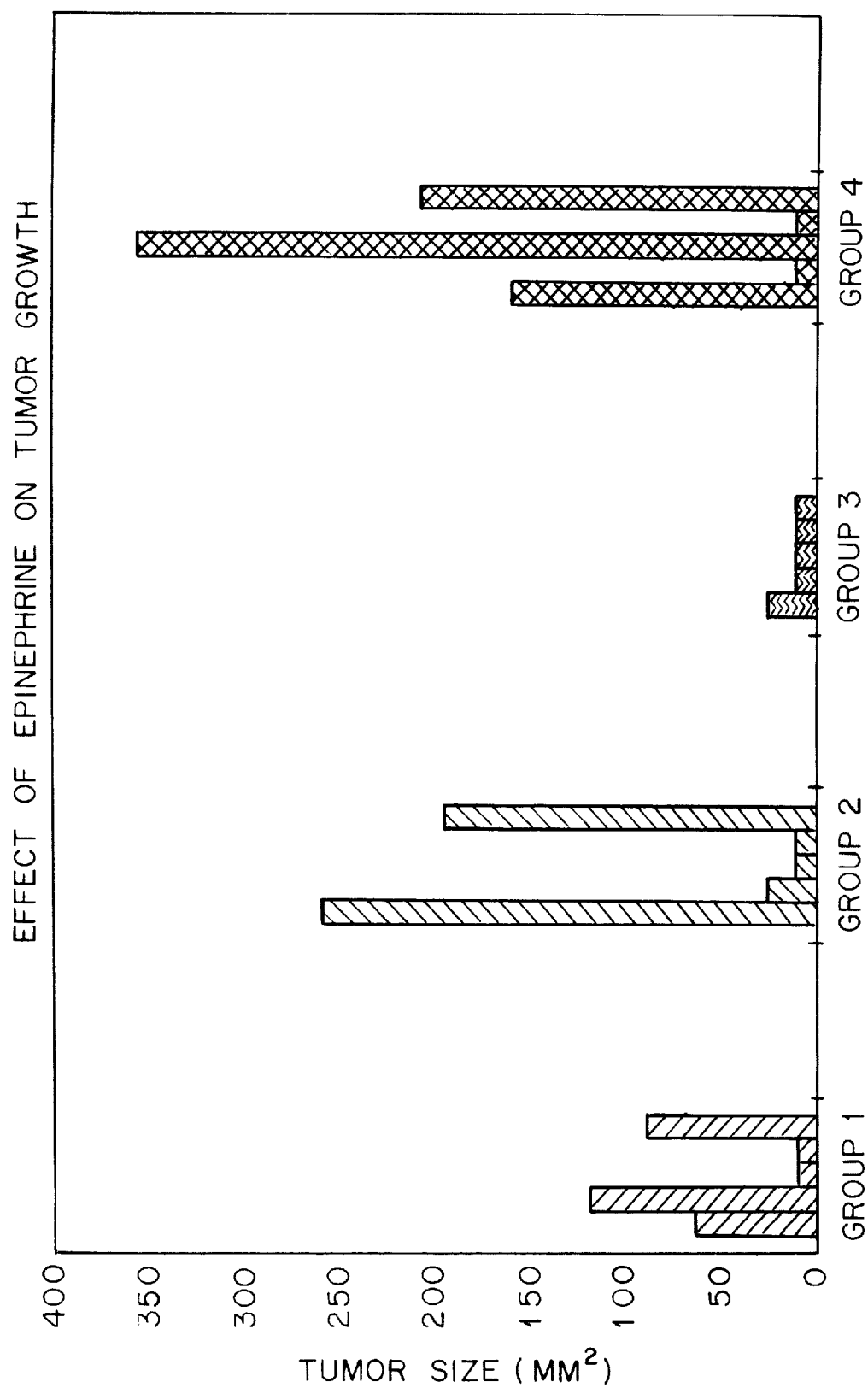

Tumor sizes were measured seven, nine, and eleven days after epinephrine injection in accordance with the method of the present invention. The results are shown in Table 2 and FIGS. 4a and 4b. FIG. 4a illustrates data obtained for individual tumor sizes nine days after epinephrine injection. FIG. 4b illustrates data obtained for individual tumor sizes 11 days after epinephrine injection. Mice without tumors were given values of 10 so as to have a visible y-axis value.

TABLE 2

EFFECT OF EPINEPHRINE ON TUMOR GROWTH

| GROUP | DOSE (mg) | DAY 7 | DAY 9 | DAY 11 |
|---|---|---|---|---|
| 1 | 0.16 | 0, 0, 0, 0, 63* | 0, 0, 64, 90, 120 | 0, 0, 0 (d)**, 0 (d), 216 |
| 2 | 0.08 | 0, 0, 0, 51, 92 | 0, 0, 25, 195, 263 | 0, 0, 90, 225, 374 |
| 3 | 0.05 | 0, 0, 0, 0, 25 | 0, 0, 0, 0, 25 | 0, 0, 0, 0, 0 (d) |
| 4 | 0.00 | 0, 0, 0, 50, 260 | 0, 0, 160, 208, 357 | 0, 0, 162, 324, 336 |

*tumor size in $mm^2$
**(d) refers to dead mouse without a tumor

The data in Table 2 indicates that mice injected with epinephrine had fewer and smaller tumors than control Group 4, on all three days presented. However, by day 18, most mice in all groups had succumbed to tumors. By day 11, four mice in the control group had tumors and one mouse had a palpable, but unmeasurable tumor, which was listed as zero in Table 1. Two of the epinephrine injected mice of group 1 had apparent tumor regressions as follows: one had died without palpable evidence of tumor, and the other had a distended abdomen and was sacrificed, but also without a palpable tumor. The regressed tumors were approximately 64 and 90 $mm^2$.

Tumor sizes have been averaged for each group of mice for days 7, 9 and 11, and the results are depicted in FIG. 5. From FIG. 5, it is apparent that the control Group 4 had a larger tumor burden than any of the epinephrine injected groups. The mice of Group 3, which had been injected with 0.05 mg epinephrine, had the smallest tumor burden.

The data set forth in Examples 1 and 2 illustrates that an intraperitoneal injection of epinephrine applied while the mammal is immobilized can significantly slow the growth of a pre-existing tumor. More specifically, a dosage amount of from about 0.05 mg to about 0.16 mg of epinephrine per body weight of 20 g injected intraperitoneally showed a temporary tumor regression of between 18–100%. A dosage amount of from about 0.02 mg to about 0.04 mg of epinephrine intravenously injected into a mammal showed a tumor regression of 20–84%.

Example 3

AKR/J mice are subcutaneously injected with 50,000 BW5147 cells in the right flank. Tumor sizes are measured by using a Vernier caliper. Metaprolol is administered into mice intravenously in an amount from about 0.1 mg to about 0.4 mg per 1000 g body weight. Immediately thereafter, the mice are injected intraperitoneally or intravenously with epinephrine chloride by following the protocol of Example 1. After injection with epinephrine, the mice are immobilized in a 50 ml plastic conical centrifuge tube of the Falcon brand, with adequate ventilation for one minute. The blood pressure of the mice is recorded. After 11 days, tumor sizes are measured for the next five days and the results are recorded. It is expected that tumor sizes for mice injected intravenously or intraperitoneally with epinephrine after an initial injection with the blocking agent metaprolol decrease in size according to patterns observed in Example 1. However, deleterious side effects on the heart associated with the use of epinephrine are expected to be significantly diminished. This example illustrates the use of metaprolol, a cardioselective andrenergic blocking agent which decreases significantly the mean aortic blood pressure of mice infused with epinephrine and thus decreases possible side effects associated with the use of epinephrine.

Example 4

This example relates to an experiment in which twenty (20), eight-month old female AKR/J mice were subcutaneously injected with 50,000 BW5147 cells in the right flank. Eleven days later, ten (10) mice were intraperitoneally injected with 0.15 milligrams of epinephrine in 0.15 milliliters of saline solution. The remaining ten (10) mice previously injected with tumor cells were not injected with epinephrine and were thus used as the control mice. No tumors were detected in both groups eleven days after the start of the experiment.

Twenty-two days after the start of this experiment, the tumor size was measured in both groups of mice, namely those which were injected with epinephrine eleven days after the beginning of the experiment and the control group which received no epinephrine. The data is set forth in Table 3.

TABLE 3

EFFECT OF EPINEPHRINE ON TUMORS
ELEVEN DAYS AFTER EPINEPHRINE INJECTION

| TUMOR SIZE* EPINEPHRINE INJECTED ($mm^2$) | TUMOR SIZE* CONTROL ($mm^2$) |
| --- | --- |
| 0 | 162 |
| 70 | 170 |
| 170 | 280 |
| 0 | 160 |
| 168 | 153 |
| 300 | 230 |
| 315 | 336 |
| 56 | 90 |
| 0 | 260 |
| 216 | 192 |
| 133.9+125.9** | 203.3 + 72.7** |

*Tumor size in $mm^2$
**Mean + Standard Deviation

As shown in Table 3 above, the epinephrine injected mice had a 33% reduction in tumor size when compared to the uninjected control mice. Further, three of the mice injected with epinephrine did not develop any tumors after the 22 day interval. While the above data does not achieve statistical significance ($p<0.15$), the above experimental data supports the fact that when applied to a cancerous mammal epinephrine produces a reduction in the tumor size.

Thus, while there have been described what are presently believed to be the preferred embodiments of the present invention, those skilled in the art will realize that other and further modifications can be made without departing from the true spirit of the invention and is intended to include all such modifications and variations as come within the scope of the claims as set forth below.

What is claimed is:

1. A method for inhibiting the growth of a lymphoma tumor which comprises administering intraperitoneally or intravenously to an immobilized mammal an effective amount of epinephrine.

2. The method of claim 1, wherein said epinephrine is added in an amount from about 0.05 mg to about 0.16 mg per 20 g body weight.

3. The method of claim 1, wherein said epinephrine is administered in an amount from about 0.02 mg to about 0.04 mg per 20 g body weight.

* * * * *